United States Patent [19]

Pope et al.

[11] 4,152,212

[45] May 1, 1979

[54] PROCESS FOR THE PURIFICATION OF GLUCURONOGLYCOSAMINOGLYCAN HYALURONATE LYASE

[75] Inventors: Derek J. Pope, Wembley; Christopher Rhodes, Gawsworth, Near Macclesfield, both of England; Steven D. Gorham, Mainz, Fed. Rep. of Germany

[73] Assignee: Biorex Laboratories Limited, London, England

[21] Appl. No.: 661,551

[22] Filed: Feb. 25, 1976

[51] Int. Cl.² .............................................. C07G 7/02
[52] U.S. Cl. ...................................... 195/66 R; 195/62
[58] Field of Search .......................... 195/62, 65, 66 R

[56] References Cited

U.S. PATENT DOCUMENTS

| 3,728,223 | 4/1973 | Kaneko et al. | 195/62 |
| 3,945,889 | 3/1976 | Mima et al. | 195/62 |

FOREIGN PATENT DOCUMENTS

| 1060513 | 3/1967 | United Kingdom | 195/66 R |
| 1425918 | 2/1976 | United Kingdom | 195/66 R |

OTHER PUBLICATIONS

*Martindale's Extra Pharmacopoeia*, 25th ed., The Pharmaceutical Press, London, (1967), pp. 885, 886.
Yang et al., "Purifcation of Bull Sperm Hyaluronidase by Concannualin-A Affinity Chromatography", *Biochem. Biophys. Acta*, vol. 391, (1975), pp. 382–387.
Borders et al., "Purification and Partial Characterization of Testicular Hyaluronidase", *Journal of Biol. Chem.*, vol. 243, No. 13, (1968), pp. 3756–3762.

*Primary Examiner*—Thomas G. Wiseman
*Attorney, Agent, or Firm*—Wenderoth, Lind & Ponack

[57] ABSTRACT

The present invention is concerned with a process for the preparation of very pure and highly active glucuronoglycosaminoglycan hyaluronate lyase by means of a special chromatographic process.

15 Claims, No Drawings

PROCESS FOR THE PURIFICATION OF GLUCURONOGLYCOSAMINOGLYCAN HYALURONATE LYASE

BACKGROUND OF THE INVENTION

In U.S. Pat. No. 3,708,575, there is disclosed a method for the treatment of cardiac arrythmias, thrombi, atherosclerosis, cerebral infarcts, cerebral thromboses, coronary thromboses and cardiac infarcts in human beings, comprising administering an effective amount of an isotonic, sterile solution of glucuronoglycosaminoglycan hyaluronate lyase (hereinafter called GL) by intravenous, intraarterial or intrathecal injection into human beings being in need of said treatment.

Many of the hyaluronidase preparations previously available have contained very large amounts of other enzymatically-active materials, in addition to the enzyme which is actually responsible for the catalysis of the hydrolysis of hyaluronic acid. The heterogeneous nature of hyaluronidase is discussed in a paper by Greiling et al. (Z. physiol. Chem., 340, 243/1965).

The hyaluronidase preparations previously available have frequently been contaminated by large and variable amounts of other enzymes, such as $\beta$-glucuronidase, N-acetyl-$\beta$-hexosaminidase, aryl sulphatase A and aryl sulphatase B.

Processes for the preparation of very pure and highly active GL have been described, for example, in our British patent specification No. 1,060,513 and also by Borders and Raftery (J. Biol. Chem. 243, 3756-3762/1968). However, these known processes are too long and complicated to be economically useful for the production of GL on a large scale, and, consequently, there is a need to provide a more economic process for the preparation of very pure and highly-active GL.

SUMMARY OF THE INVENTION

According to the present invention, there is provided a process for the preparation of very pure and highly-active GL, wherein a solution of crude enzyme is first contacted with a cross-linked polyacrylic divinyl-benzene resin containing carboxyl groups as active groups (for example, the resin available under the Registered Trade Mark "Amberlite CG-50"), the absorbed enzyme is then eluted from the resin, the eluate fractions which are rich in the desired enzyme are dialysed against a saturated aqueous solution of ammonium sulphate, the enzyme concentrate obtained then contacted with a cross-linked dextran gel containing active carboxymethyl groups (for example, that available under the Registered Trade Mark "CM-Sephadex"), followed by elution of the gel to give a solution of very pure and highly active GL.

Alternatively, the enzyme concentrate from the ammonium sulphate dialysis step can be contacted with a cross-linked dextran gel which does not contain active carboxymethyl groups (for example, that available under the Registered Trade Mark "Sephadex G-75" and "Sephadex G-100"), followed by elution of the gel. The solution of highly active GL thus obtained can, if desired, be further purified by contacting with a cross-linked dextran gel containing active carboxymethyl groups (for example, CM-Sephadex), followed by elution of the gel.

The solution of crude enzyme used as starting material can be prepared in known manner from any source which is rich in the desired enzyme. Because of ready availability, it is preferred to use animal testes, such as ox testes, for the preparation of the solution of the crude enzyme but other materials, such as liver lysozomes, can also be used.

The carboxyl group-containing resin used in the first stage of the purification is preferably equilibrated at ambient temperature with a 0.1M phosphate buffer (pH 6.0) and the crude enzyme is preferably dissolved in the same buffer. The resin can be used in a column or this stage can be carried out by a batch process in which the resin is contacted with the enzyme solution in a vessel equipped with stirring means. After washing the resin with 0.1M phosphate buffer (pH 6.0), it is then eluted with 0.3M phosphate buffer (pH 7.7) and the enzyme-rich fractions collected and pooled. The whole of this stage of the process can conveniently be carried out at ambient temperature.

The enzyme-enriched solution thus obtained is then concentrated by dialysis against a concentrated aqueous solution of ammonium sulphate until the volume of the enzyme solution has decreased, for example, by about two thirds. This dialysis is preferably carried out at a temperature below ambient temperature, for example, at about 4° C. The enzyme-active precipitate obtained in the dialysis bag can then be isolated, for example, by centrifuging at ambient temperature.

This precipitate is then dissolved in 0.1M aqueous sodium chloride solution and applied to a column of the cross-linked dextran gel which does not contain active carboxymethyl groups at about 4° C. which has been equilibrated with 0.1M aqueous sodium chloride solution. The gel is then eluted with 0.1M aqueous sodium chloride solution and the enzyme-rich fractions collected and pooled.

The precipitate from the dialysis step or the enzyme-rich fractions from the treatment step with the cross-linked dextran gel which does not contain active carboxymethyl groups can be dissolved in 0.1M acetate buffer (pH 5.0) and applied to a column of cross-linked dextran gel containing active carboxymethyl groups at about 4° C. which has been equilibrated with 0.1M acetate buffer (pH 5.0). The gel is then eluted with 1.0M acetate buffer (pH 5.0) and the enzyme-rich fractions collected and pooled.

Similarly, the dialysis concentrate can be dissolved in 0.1M acetate buffer (pH 5.0), applied at about 4° C. to a cross-linked dextran gel containing active carboxymethyl groups which has been equilibrated with 0.1M acetate buffer (pH 5.0) and the gel then eluted with 1.0M acetate buffer (pH 5.0).

By means of the process according to the present invention, it is possible to obtain a more than 90 fold purification of the enzyme activity and the overall recovery of the enzyme may be over 40%.

The following Examples are given for the purpose of illustrating the present invention:

EXAMPLE 1

Stage I: Ion exchange chromatography (a) A column of "Amberlite CG-50" (2.2 × 13 cm.) was equilibrated at ambient temperature with a 0.1M phosphate buffer (pH 6.0). 421 ml. of a solution of the crude enzyme in the same buffer (containing 7.46 g. protein and 255 I.U. of enzyme/mg. protein, i.e., 1,902,300 I.U. enzyme) was applied to the column, which was then washed with 1 liter 0.1M phosphate buffer (pH 6.0). The column was subsequently eluted at ambient temperature with 0.3M phosphate buffer (pH 7.7) at a flow rate of about 180 ml./hour, the eluate being collected in fractions. The results obtained are set out in the following Table I:

TABLE I

| Fraction | vol. (ml.) | Protein conc. (mg./ml.) | % protein recovery | spec. act. (IU/mg. protein) | total activity (IU) | % yield of enzyme |
|---|---|---|---|---|---|---|
| A | 38 | 1.12 | 4.2 | 580 | 24685 | 8.23 |
| B | 36 | 2.0 | 7.2 | 2250 | 162000 | 54 |
| C | 13 | 1.01 | 1.3 | 356 | 4674 | 1.56 |

(b) The process described above under (a) was repeated but with the use of a larger column (4.2 × 30 cm.) of "Amberlite CG-50." It was found that the yield of enzyme obtained was higher than when using the smaller column. The results obtained are set out in the following Table II:

TABLE II

| Fraction | vol. (ml.) | protein conc. (mg./ml.) | % protein recovery | spec.act. (IU/mg. protein) | total activity (IU) | % yield of enzyme |
|---|---|---|---|---|---|---|
| A | 132 | 1.48 | 2.62 | 797 | 155733 | 8.2 |
| B | 206 | 2.57 | 7.09 | 2529 | 1338903 | 70.4 |
| C | 194 | 1.02 | 2.65 | 343 | 67873 | 3.6 |

Stage II: Dialysis

The active fraction B from Stage I was concentrated by dialysis of the solution against a saturated aqueous solution of ammonium sulphate at 4° C. until the volume of the active fraction had decreased by two thirds (equivalent to about 60 – 70% saturated ammonium sulphate solution in the dialysis bag). The enzyme-active precipitate obtained from the dialysis bag was then isolated by centrifuging at ambient temperature for 3 minutes at 4000 rpm.

Stage III: Gel filtration

A column of "Sephadex G-75" (4.2 × 75 cm.) was equilibrated at 4° C. with a 0.1M aqueous sodium chloride solution. The isolated enzyme material obtained from Stage II was dissolved in 15 ml. 0.1M aqueous sodium chloride solution and applied directly to the gel column. The column was then eluted with 0.1M aqueous sodium chloride solution at a rate of 50 ml./hour, the eluate being collected in fractions and the enzyme-rich fractions were pooled. The enzyme-rich pooled fractions contained 40.3% of the original enzyme activity and the enzyme activity showed a 92.5 fold purification.

The overall results of the three-stage purification are set out in the following Table III:

EXAMPLE 2

Stage I: Ion exchange chromatography

A column of "Amberlite CG-50" (4.4 × 60 cm.) was equilibrated at ambient temperature with a 0.1M phosphate buffer (pH 6.0). 550 ml. of a solution of the crude enzyme in the same buffer (containing 5.98 g. protein and 340 I.U. of enzyme/mg. protein, i.e., 2.03 × 10$^6$ I.U. enzyme) were applied to the column, which was then washed with 2.5 liters 0.1M phosphate buffer (pH 6.0). The column was subsequently eluted at ambient temperature with 0.3M phosphate buffer (pH 7.7) at a flow rate of 30 ml./hour, the eluate being collected in fractions. The enzyme-rich fractions were pooled.

Stage II: Dialysis

The active fraction from Stage I was concentrated by dialysis of the solution against a saturated aqueous solution of ammonium sulphate at 4° C., in the manner described in Example 1.

Stage III: Gel filtration

A column of "Sephadex G-75" (4.4 × 72 cm.) was equilibrated at 4° C. with a 0.1M aqueous sodium chloride solution. The isolated enzyme material obtained from Stage II was dissolved in 18.5 ml. 0.1M aqueous sodium chloride solution and applied directly to the gel column. The column was then eluted with 0.1M aqueous sodium chloride solution at a rate of 20 ml./hour, the eluate being collected in fractions. The enzyme-rich fractions were pooled.

Stage IV: Ion exchange chromatography

A column of "CM-Sephadex" (13 × 1.5 cm.) was equilibrated at 4° C. with a 0.1M acetate buffer (pH 5.0). The enzyme-rich fractions from Stage III were applied to the column, which was then washed with 0.42M acetate buffer (pH 5.0). The column was subsequently eluted at 4° C. with 0.85M acetate buffer (pH 5.) and the eluate collected in fractions. The pooled enzyme-rich fractions contained 23% of the original enzyme activity and the enzyme activity showed an 88.3 fold purification.

The overall results of the 4 stage purification are set out in the following Table IV:

TABLE IV

| Step | total protein (mg.) | specific activity (I.U./mg. protein) | total activity (I.U.) | relative activity | Yield of enzyme activity (%) |
|---|---|---|---|---|---|
| Crude enzyme | 5,980 | 340 | 2.03 × 10$^6$ | 1 | 100 |
| "Sephadex G-75" | 57 | 15,000 | 8.55 × 10$^5$ | 44 | 42 |
| "CM Sephadex" | 16 | 30,000 | 4.8 × 10$^5$ | 88.3 | 23 |

TABLE III

| Step | Volume (ml) | protein conc. (mg./ml.) | Total protein (mg.) | % protein recovery | Specific activity (I.U./mg. protein) | Total activity (IU) | Relative activity | Yield of enzyme activity % |
|---|---|---|---|---|---|---|---|---|
| Crude enzyme | 421 | 17.72 | 7460 | | 255 | 1,902,300 | 1.0 | 100 |
| "Amberlite CG-50" | 206 | 2.57 | 529.4 | 7.09 | 2529 | 1,338,903 | 9.9 | 70.4 |
| Ammonium sulphate concentration | 19.3 | 19.0 | 366.7 | 4.92 | 4000 | 1,466,800 | 15.7 | 77.1 |
| "Sephadex G-75" | 36.5 | 0.89 | 32.5 | 0.44 | 23596 | 766,516 | 92.5 | 40.3 |

EXAMPLE 3

Stage I: Ion exchange chromatography

A column of "Amberlite CG-50" (3.5 × 32 cm.) was equilibrated at ambient temperature with a 0.1M phosphate buffer (pH 6.0). 110 ml. of a solution of the crude enzyme in the same buffer (containing 585 mg. protein and 300 I.U. of enzyme/mg. protein, i.e., 175,500 I.U. enzyme) were applied to the column, which was then washed with 700 ml. 0.1M phosphate buffer (pH 6.0). The column was subsequently eluted at ambient temperature with 0.3M phosphate buffer (pH 7.7) at a flow rate of 28.ml./hour and the elute was collected in fractions. The enzyme-rich fractions were pooled.

Stage II: Dialysis

The active fraction from stage I was concentrated by dialysis of the solution against a saturated aqueous solution of ammonium sulphate at 4° C., as described in Example 1.

Stage III: Gel filtration

A column of "Sephadex G-100" (3.2 × 55 cm.) was equilibrated at 4° C. with a 0.1M aqueous sodium chloride solution. The isolated enzyme material obtained from Stage II was dissolved in 10 ml. 0.1M aqueous sodium chloride solution and applied directly to the gel column. The column was then eluted with 0.1M aqueous sodium chloride solution at a rate of 25 ml./hour and the eluate collected in fractions. The enzyme-rich fractions were pooled.

Stage IV: Ion exchange chromatography

A column of "CM Sephadex" (1.6 × 11 cm.) was equilibrated at 4° C. with a 0.14M acetate buffer (pH 5.0). The enzyme-rich fractions from Stage III were applied to the column, which was then washed with 0.42M acetate buffer (pH 5.0). The column was subsequently eluted with 0.85M acetate buffer (pH 5.0) and the eluate collected in fractions. The pooled enzyme-rich fractions contained 32.8% of the original enzyme activity and the enzyme activity showed a 38.3 fold purification.

The overall results of the 4 stage purification are set out in the following Table V:

TABLE V

| Step | total protein (mg.) | specific activity (I.U./mg. protein) | total activity (I.U.) | relative activity | yield of enzyme activity (%) |
|---|---|---|---|---|---|
| Crude enzyme | 585 | 300 | $1.75 \times 10^5$ | 1 | 100 |
| Amberlite CG-50 | 70 | 2,020 | $1.41 \times 10^5$ | 6.74 | 80.5 |
| Sephadex G-100 | 19 | 5,000 | $9.5 \times 10^4$ | 16.7 | 54 |
| CM Sephadex | 5 | 11,500 | $5.75 \times 10^4$ | 38.3 | 32.8 |

The strength of the GL in IU was determined by the international standard assay procedure accepted by the World Health Organisation (see J. H. Humphrey, Bull. W.H.O., 16, 291/1957) for the assay of hyaluronidase (see also U.S. Pharmacopeia, 15th revision, p.329/1955) but replacing the 0.1M phosphate buffer — 0.15M NaCl, pH 7.0 by 0.1M sodium acetate — 0.15M NaCl, pH 6.0 buffer and using ox serum instead of human serum, all other conditions being the same.

The GL obtained by the process according to the present invention is immunochemically pure and sterile and substantially free of bovine protein, pyrogenic materials and antigenic components.

The GL obtained by the process according to the present invention can be used for the treatment of circulatory diseases in humans, including cardiac arrhythmias, thrombi, coronary thromboses, cardiac infarcts, cardiac arrest, stroke, heart block, atherosclerosis and cerebral thromboses, as well as for the treatment of auto-immune diseases in humans in which it is desirable to transport entigens to the lymphatic system to create anti-bodies, for example ulcertaive colitis and Crohn's disease (i.e., regional ileitis).

The GL is administered systemically, for example, intravenously, intraarterially, intrathecally, subcutaneously or intramuscularly, in the form of an isotonic sterile solution. The amount of GL administered depends upon the severity of the disease to be treated and can be from 5000 to $10^6$ IU and preferably from 20,000 to $10^6$ IU.

We claim:

1. A process for the preparation of very pure and highly active glucuronoglycosaminoglycan hyaluronate lyase, which comprises contacting a crude lyase-containing solution with a cross-linked polyacrylic divinyl-benzene resin containing carboxyl groups as active groups, eluting the absorbed lyase from the resin, dialyzing the eluate fractions which are rich in the desired lyase against a saturated aqueous solution of ammonium sulphate and further purifying the enzyme concentrate thus obtained by contacting said concentrate with a cross-linked dextran gel containing active carboxymethyl groups, followed by elution of the gel to give a solution of the desired lyase.

2. A process according to claim 1, wherein the cross-linked polyacrylic divinyl-benzene resin is equilibrated at ambient temperature with a 0.1M phosphate buffer (pH 6.0).

3. A process according to claim 1, wherein the crude enzyme is applied to the cross-linked polyacrylic divinyl-benzene resin in a 0.1M phosphate buffer (pH 6.0).

4. A process according to claim 1, wherein the cross-linked polyacrylic divinyl-benzene resin is washed with a 0.1M phosphate buffer (pH 6.0) and the lyase is then eluted with a 0.3M phosphate buffer (pH 7.7).

5. A process according to claim 1, wherein the dialysis is carried out at a temperature of about 4° C..

6. A process according to claim 1, wherein the dialysis concentrate is dissolved in 0.1M acetate buffer (pH 5.0), applied at about 4° C. to a cross-linked dextran gel containing active carboxymethyl groups which has been equilibrated with 0.1M acetate buffer (pH 5.0) and the gel then eluted with 1.0M acetate buffer (pH 5.0).

7. A process for the preparation of very pure and highly active glucuronoglycosaminoglycan hyaluronate lyase, which comprises contacting a crude lyase-containing solution with a cross-linked polyacrylic divinyl-benzene resin containing carboxyl groups as active groups, eluting the adsorbed lyase from the resin, dialyzing the eluate fractions which are rich in the desired lyase against a saturated aqueous solution of ammonium sulphate and further purifying the enzyme concentrate thus obtained by contaning said concentrate with a cross-linked dextran gel which does not contain active carboxymethyl groups, followed by elution of the gel to give a solution of the desired lyase.

8. A process according to claim 7, wherein the eluate obtained from the cross-linked dextran gel which does not contain active carboxymethyl groups is further contacted with a cross-linked dextran gel containing active carboxymethyl groups, followed by elution of the gel to give a solution of the desired lyase.

9. A process according to claim 7, wherein the cross-linked polyacrylic divinyl-benzene resin is equilibrated at ambient temperature with a 0.1M phosphate buffer (pH 6.0).

10. A process according to claim 7, wherein the crude enzyme is applied to the cross-linked polyacrylic divinyl-benzene resin in a 0.1M phosphate buffer (pH 6.0).

11. A process according to claim 7, wherein the cross-linked polyacrylic divinyl-benzene resin is washed with a 0.1M phosphate buffer (pH 6.0) and the lyase is then eluted with a 0.3M phosphate buffer (pH 7.7).

12. A process according to claim 7, wherein the dialysis is carried out at a temperature of about 4° C.

13. A process according to claim 7, wherein the dialysis concentrate is dissolved in 0.1M aqueous sodium chloride solution and applied at about 4° C. to the cross-linked dextran gel which does not contain active carboxymethyl groups and which has been equilibrated with 0.1M aqueous sodium chloride solution.

14. A process according to claim 7, wherein the cross-linked dextran gel which does not contain active carboxymethyl groups is eluted with 0.1M aqueous sodium chloride solution.

15. A process according to claim 7, wherein the fractions from the treatment step with the cross-linked dextran gel which does not contain active carboxymethyl groups are dissolved in 0.1M acetate buffer (pH 5.0), applied at about 4° C. to a cross-linked dextran gel containing active carboxymethyl groups which has been equilibrated with 0.1M acetate buffer (pH 5.0) and the gel then eluted with 1.0M acetate buffer (pH 5.0).

* * * * *